United States Patent
Bonrath et al.

(10) Patent No.: US 7,897,822 B2
(45) Date of Patent: Mar. 1, 2011

(54) PROCESS FOR UBIQUINONE INTERMEDIATES

(75) Inventors: Werner Bonrath, Freiberg (DE); Francesco Pace, Stein (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/097,836

(22) PCT Filed: Dec. 8, 2006

(86) PCT No.: PCT/EP2006/011781
§ 371 (c)(1),
(2), (4) Date: Nov. 4, 2008

(87) PCT Pub. No.: WO2007/071329
PCT Pub. Date: Jun. 28, 2007

(65) Prior Publication Data
US 2009/0227819 A1 Sep. 10, 2009

(30) Foreign Application Priority Data
Dec. 20, 2005 (EP) .................................. 05027850

(51) Int. Cl.
*C07C 33/04* (2006.01)
(52) U.S. Cl. ....................................................... 568/874
(58) Field of Classification Search ................ 568/874
See application file for complete search history.

(56) References Cited

U.S. PATENT DOCUMENTS

| 3,082,260 | A | 3/1963 | Tedeschi et al. |
| 3,709,946 | A | 1/1973 | Tedeschi et al. |
| 6,828,468 | B2 * | 12/2004 | Ansmann et al. ............. 568/874 |

FOREIGN PATENT DOCUMENTS

| EP | 0 816 321 | 1/1998 |
| EP | 1 256 560 | 11/2002 |
| JP | 54-98707 | 8/1979 |

OTHER PUBLICATIONS

Database Caplus [Online] Chemical Abstract Service, Abstract of Takeshi et al., "Ketone Ethynylation in 1, 3-Dialkyl-2-Imidazolidinones", 1 Page, (Aug. 3, 1979).
Nazarov, I. N. et al., "The Synthesis of Fatty Acids and Alcohols from Tertiary Vinylcarbinols", Journal of General Chemistry of the USSR, vol. 30, No. 1, pp. 467-473, (Feb. 1960).
International Search Report for PCT/EP2006/011781, mailed May 14, 2007.
Written Opinion of the International Searching Authority for PCT/EP2006/011781, mailed May 14, 2007.

* cited by examiner

*Primary Examiner* — Sikarl A Witherspoon
(74) *Attorney, Agent, or Firm* — Nixon & Vanderhye P.C.

(57) ABSTRACT

A process for the preparation of terminally ethylenically unsaturated isopolyprenols characterized in that a carbonyl compound is reacted with ethine in the presence of ammonia and low amounts of an alkaline metal hydroxide and, if desired, the terminally acetylenically unsaturated isopolyprenol obtained is partially hydrogenated in the presence of a catalyst suitable for selective hydrogenation.

6 Claims, No Drawings

PROCESS FOR UBIQUINONE INTERMEDIATES

This application is the U.S. national phase of International Application No. PCT/EP2006/011781, filed Dec. 8, 2006, which designated the U.S. and claims priority to Europe Application No. 05027850.6, filed Dec. 20, 2005, the entire contents of each of which are hereby incorporated by reference.

The present invention relates to a process for the preparation of ubiquinone intermediates. More precisely, the present invention relates to the preparation of isopolyprenols.

Ubiquinones are prenylated quinones which are present in nearly all organisms, in plants and animals including humans, and known since 1956. They are part of the inner membrane of mitochondria and bacterial membranes serving as transmitters of electrons and protons in the respiratory chain where they are reversibly transformed into corresponding hydroquinones (ubiquinols) via semiquinones.

Ubiquinones, also known as coenzymes Q (CoQ), are designated according to the number of the isoprenyl units of their side chain Q-1, Q-2, Q-3, etc. (or CoQ1, CoQ2, CoQ3, etc.) or according to the number of the carbon atoms of their side chain U.-5, U.-10, U.-15, etc. In *Escherichia coli* Q-1 to Q-8 have been found, in fish Q-9 and in rat Q-11 and Q-12. In most mammals including humans Q-10 is predominant and, therefore, has attracted most interest.

Ubiquinones, especially the higher ones, CoQ8 to CoQ12, and particularly CoQ10, are widely used, e.g., in the treatment and prevention of various diseases such as heart and neurological diseases, in cosmetics and as food or dietary supplements. Ubiquinoles as part of the ubiquinone/ubiquinole redox-system are natural antioxidants.

O. Isler and co-workers were the first to synthesize U.-45 (Q-9) and U.-50 (Q-10) from 5-methyl-2,3-dimethoxy-hydroquinone and solanesol (contained in tobacco leaf) or the corresponding isoprenoid compound obtained by extending solanesol by one isoprenyl unit, respectively, in diethyl ether in the presence of $ZnCl_2$ as catalyst and oxidizing the resulting condensation product with $Ag_2O$ (Helv. Chim. Acta 42, 2616-2621 [1959]).

H. Fukawa et al. in U.S. Pat. No. 3,549,668 describe the preparation of coenzymes $Q_9$-$Q_{12}$. Solanesol or isoprenyl alcohols corresponding to $Q_9$, $Q_{11}$ and $Q_{12}$, extracted from Silkworm feces or mulberry leaves, are condensed in the presence of $ZnCl_2$, $AlCl_3$ and $BF_3$ ether complex with 5-methyl-2,3-dimethoxy-hydroquinone or its 4-acyl derivative and the ubihydroquinones obtained were oxidized according to the methods described by Isler et al.

According to O. Isler et al, the carbonyl compound (compound VI) in anhydrous ether is reacted with a high amount of sodium acetylide (prepared from sodium and ethyne) in liquid ammonia during 15 hours to yield the dehydroisodecaprenol (compound VII, corresponding to present compound Ia with n=8).

Also H. Fukawa et al. in U.S. Pat. No. 3,549,668 describe that the $C_{50}$-ethynyl carbinol is prepared by reaction of high amounts of sodium acetylide (prepared from sodium and acetylene) with the carbonyl compound in liquid ammonia during 20 hours.

However, it has now be found surprisingly that dehydroisopolyprenols can be produced easily in high yield and purity by reacting the carbonyl compound with ethine in the presence of ammonia and comparatively low amounts of an alkaline metal hydroxide.

Apart form the fact that the method in accordance with the present invention can be conducted with or without an organic solvent in the presence of gaseous or liquefied ammonia the use of comparatively low amounts of an alkaline metal hydroxide is advantageous compared with the use of sodium acetylide in liquid ammonia. Nevertheless, high yields of the dehydroisopolyprenol are obtained in high purity in shorter reaction time. The dehydroisopolyprenol can then be partially hydrogenated in a manner known per se, e.g., in the presence of a catalyst suitable for selective hydrogenation to yield the corresponding isopolyprenol.

Therefore, the present invention relates to a process for the preparation of iso-polyprenols of the formula

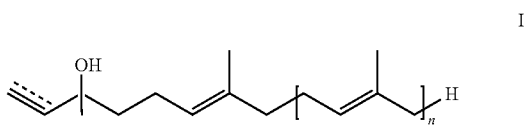

I wherein n is an integer of 6-10 and the dotted line means that a line is present or not, which process is characterized in that a carbonyl compound of formula

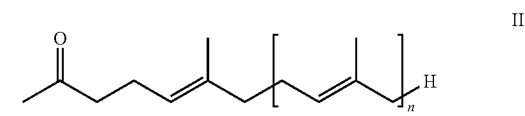

II is reacted with ethine in the presence of ammonia and low amounts of an alkaline metal hydroxide and, if desired, the resulting ethinol of formula

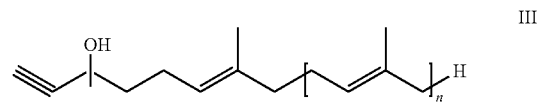

III is partially hydrogenated in the presence of a catalyst suitable for the selective hydrogenation of the triple bond to a double bond.

Formula I comprises compounds of formula Ia which are terminally acetylenically unsaturated and of formula Ib which are terminally ethylenically unsaturated.

The alkali metal hydroxide catalyst used in the process of the present invention is sodium or potassium hydroxide, of which the latter is preferred. The alkali metal hydroxide is conventionally used as a solution in deionized water of up to 50%, w/v, preferably in a concentration of 40-45%, w/v.

The molar ratio of the alkali metal hydroxide to the carbonyl compound in the reaction mixture is generally from about 0.3:1 to about 5.0:1, preferably from about 0.35:1 to about 1.5:1.

The molar ratio of ethine to the carbonyl compound of formula II in the process of the present invention is generally from about 2:1 to about 6:1. The ethynylation is preferably effected at temperatures form about room temperature (about 20° C.) to about 35° C.

The reaction can be carried out in an organic solvent, preferably a non-polar, e.g. an ether, such as diethyl or methyl tert-butyl ether (MTBE), an aliphatic hydrocarbon, such as n-hexane, or an aromatic hydrocarbon such as toluene, or in mixtures thereof. Alternatively, by using liquefied ammonia as the reaction solvent the process of the present invention avoids the use of organic solvents, which is advantageous.

Instead of using gaseous ammonia and an organic solvent the ammonia is maintained in liquid state by appropriate choice of temperature and pressure whereby at the same time an adequate ethine pressure must also be provided and sustained in the reaction vessel.

The reaction temperature is conveniently in the range of from about 0° C. to about 40° C. The pressure is maintained at an appropriate value, depending on the reaction temperature, which is suitably from about 5 bar to about 20 bar (about 0.5 Mpa to about 2 Mpa).

The process of the present invention can be carried out in a manner known per se for the ethynylation of carbonyl compounds. Typically, for batchwise operation, the desired amounts of aqueous alkali metal hydroxide solution, the carbonyl compound and ethine are introduced into a reactor. The reactor is then sealed and inertized by repeatedly filling with ammonia and venting. Finally, a desired amount of ammonia is introduced into the reactor. Acetylene is then also added in the desired amount with stirring to start the reaction. During the reaction further acetylene may be added semi-continuously to maintain a constant ketone: acetylene molar ratio. The reaction time is in the range of 0.25-5 hours, preferably 1-2 hours.

Alternatively the process in accordance with the present invention can be carried out continuously, e.g., by continuous addition of a mixture of ethine and ammonia together with the carbonyl compound and aqueous alkali hydroxide solution into a reactor, e g., a plug-flow reactor, and continuous withdrawal of the product.

The selective hydrogenation of the compounds of formula I$a$ to compounds of formula I$b$ can be achieved in a manner known per se, e.g., by the use of Pd catalysts, preferably Lindlar catalysts, such as Pd/Pb/CaCO$_3$, Pd/BaSO$_4$ or Pd/PbO/CaCO$_3$ (Helv. Chim. Acta 35, 446 [1952]; Fieser, Reagents for Organic Synthesis [New York, 1967] p. 566), if desired with additional modifiers, which catalysts are commercially available.

The invention is further illustrated by the following non-limiting examples.

EXAMPLE 1

In a 2 l autoclave 80 g (114.43 mmol, 96% purity) of the C$_{48}$-ketone of formula II (n=8) were dissolved in 200 g (230 ml) of toluene. After addition of 5.20 ml of a solution of 7.088 g KOH (53,81 mmol, 42.6%, w/w) in deionized water the reaction vessel was evacuated and refilled with 351 g of ammonia (20,61 mol). At a temperature of 20° C. ethine was added to the reactor under stirring at 1200 rpm until an internal pressure of 15.9 bar was reached. During the reaction ethine was constantly added to the reaction mixture (semi-batch). After the reaction was complete (5 hours) ammonia was evaporated and the reaction mixture was neutralized with 100 ml of 50% aqueous acetic acid (pH control). The crude product, ethinol of formula II (n=8), dehydroisodecaprenol, was washed with 1.5 l of water, dried over sodium sulfate and concentrated at 40° C. under reduced pressure (10 mbar). Yield: 76.2 g (95.5%).

EXAMPLES 2-5

The conditions and results of additional experiments, carried our in analogy to the procedure of Example 1, are summarized below. In all experiments 10 g (0.013 mmol) of the C$_{48}$-ketone were used; the molar ratio KOH/C$_{48}$-ketone was 2.33 (not optimized) and the ratio C$_{48}$-ketone/NH$_3$ was 0.0285 (not optimized). MTBE=methyl tert-butyl ether.

| Example | Solvent/ml | Reaction Time [h] | Conversion [%] | Yield [%] |
|---|---|---|---|---|
| 2 | n-hexane/230 | 2 | 96.5 | 90 |
| 3 | None | 1 | 98.2 | 91 |
| 4 | MTBE | 1 | 98.4 | 94 |
| 5 | toluene/230 | 1 | 98.8 | 94 |

EXAMPLE 6

In a 0.5 l autoclave 109.8 l of dehydroisodecaprenol (purity 69.41%, w/w, 109.32 mmol) were dissolved in 193 g (223 ml) of toluene. 500 mg of a Lindlar catalyst (Degussa, CE 407 R/D 5% Pd+3.5% Pb, 20052500) and 20.6 mg of Tegochrome 22 (T. Goldschmidt Ltd., 2,2'-ethylenedithiodiethanol) were added. After inertisation of the autoclave with nitrogen the mixture was heated up to 85° C. At a temperature of approximately 60° C. 3 bara hydrogen were added, the mixture was heated to 85° C. and after the reaction was complete (1 hour) the autoclave was cooled to room temperature and the catalyst was separated from the reaction mixture. The toluene was distilled off at a temperature of 40° C. under reduced pressure (10 to 0.02 mbar), yielding 78.2 g (99.2%) of crude isodecaprenol (purity 97%, w/w).

The invention claimed is:

1. A process for the preparation of iso-polyprenols of the formula

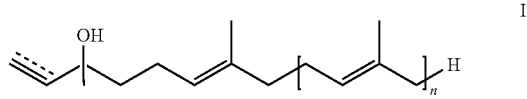

I wherein n is an integer of 6-10 and the dotted line means that a line is present or not, and wherein the process comprises reacting a carbonyl compound of formula

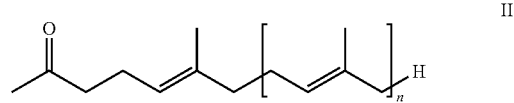

II with ethine in the presence of ammonia and an alkaline metal hydroxide in a non-polar, aprotic organic solvent or in the absence of organic solvents and optionally thereafter partially hydrogenating the resulting ethinol of formula

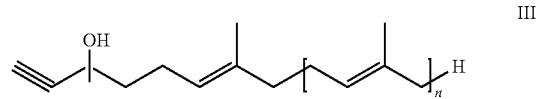

III in the presence of a catalyst suitable for the selective hydrogenation of the triple bond to a double bond, wherein the molar ratio of the alkali metal hydroxide to the carbonyl compound is in the range of 0.3:1 to about 5.0:1.

2. The process of claim 1, wherein the alkali metal hydroxide is potassium hydroxide.

3. The process of claim 1, wherein an aqueous solution of the alkaline metal hydroxide is used.

4. The process of claim 1, wherein the carbonyl compound is ethinylated in the presence of liquefied ammonia.

5. The process of claim 1, wherein the hydrogenation catalyst is a Lindlar catalyst.

6. The process of claim 1, wherein n is 8.

* * * * *